(12) United States Patent
Bayer et al.

(10) Patent No.: US 9,394,512 B2
(45) Date of Patent: Jul. 19, 2016

(54) METHOD FOR GROWING MYCOLOGICAL MATERIALS

(71) Applicants: Eben Bayer, Troy, NY (US); Gavin R. McIntyre, Troy, NY (US)

(72) Inventors: Eben Bayer, Troy, NY (US); Gavin R. McIntyre, Troy, NY (US)

(73) Assignee: ECOVATIVE DESIGN LLC, Green Island, NY (US)

( * ) Notice: Subject to any disclaimer, the term of this patent is extended or adjusted under 35 U.S.C. 154(b) by 37 days.

(21) Appl. No.: 14/712,546

(22) Filed: May 14, 2015

(65) Prior Publication Data

US 2015/0247115 A1 Sep. 3, 2015

Related U.S. Application Data

(60) Division of application No. 13/492,230, filed on Jun. 8, 2012, and a continuation-in-part of application No. 13/454,856, filed on Apr. 24, 2012.

(51) Int. Cl.
*C12N 1/14* (2006.01)

(52) U.S. Cl.
CPC ....................................... *C12N 1/14* (2013.01)

(58) Field of Classification Search
None
See application file for complete search history.

(56) References Cited

U.S. PATENT DOCUMENTS 6,329,185 B1 * 12/2001 Kofod .................. A23K 1/1653
435/183
2009/0241623 A1 * 10/2009 Matano ................ A01K 1/0152
71/9

FOREIGN PATENT DOCUMENTS

WO   WO 2010/005476   *   1/2010   ............... C12N 1/00

OTHER PUBLICATIONS

Biotechnology for Agro-Industrial Residues, (2009).*

* cited by examiner

*Primary Examiner* — Suzanne M Noakes
*Assistant Examiner* — Stephen Chong
(74) *Attorney, Agent, or Firm* — Francis C. Hand; Carella, Byrne, et al

(57) ABSTRACT

The method of growing the basidiomycete mycelium includes inoculating a substrate that promotes the growth and differentiation of basidiomycete mycelium without supporting the production of a basidiocarp with a vegetative mycelium and thereafter incubating the inoculated substrate in a first incubation period at controlled temperature, humidity, light and carbon dioxide levels followed by a finishing incubation period.

18 Claims, No Drawings

METHOD FOR GROWING MYCOLOGICAL MATERIALS

This application claims the benefit of Provisional Patent Application 61/494,477.

This application is a Division of pending U.S. patent application Ser. No. 13/492,230, filed Jun. 8, 2012 which is a Continuation-in-Part of pending U.S. patent application Ser. No. 13/454,856, filed Apr. 24, 2012.

This invention relates to a method for growing mycological materials.

As is known from published United States Patent Application 2008/0145577, use can be made of a fungus to form composite materials by mixing an inoculum including a pre-selected fungus with discrete particles and a nutrient material capable of being digested by the fungus. It is also known from U.S. Pat. No. 8,001,719 to enclose and grow a fungal primordium in a mold to obtain a mass of fungal tissue in the form of low density chitinous material.

Briefly, this invention provides an engineered substrate for the production of mycological materials as well as an improvement on the method described in published US Patent Application 2008/0145577 for the production of mycological materials. In this regard, the method also provides for an optimal incubation environment to promote various types of mycelium physiology on the substrate.

In accordance with the invention, the substrate is comprised of both nutritional and non-nutritional particles or fiber, which promote the growth and differentiation of basidiomycete mycelium but does not support the production of a basidiocarp (fruiting body or mushroom). A nutritional particle or fiber is defined as providing an easily accessible carbon source for the fungal mycelium; this includes simple sugars (dextrose, cellulose, maltose), carbohydrates (maltodextrin, starch), and lignin. These nutritional carbon sources can be used either in their raw form, as in a reagent grade chemical, or as the prevailing plant matter component. A prevalent carbon source is defined as comprising more than 20% of dry mass, and a nutritional particle must contain at least one dominate carbon source.

The summation of carbon source composition, such as a combination of a starch and lignin, does not meet the criteria since basidiomycetes can alone breakdown one carbon source at a time and enzymatic repression has been found to promote singular carbon source selection.

NUTRITIONAL PARTICLE EXAMPLE

Softwood sawdust, such as Scot Pine or Birch, range in cellulosic starch composition by greater than 40% by dry weight. Hemicelluloses are also prevalent, which serve as a secondary carbon source for the fungal mycelium, and typically compose more than 20% of the tree.

A non-nutritional particle or fiber either offers a carbon source accessible by the fungal mycelium but is less than 20% of the material's total dry mass, or the material offers no nutritional value. This particle or fiber could be carbon deficient, such as the silicon dioxide found in rice hulls, or offer a carbon source that is not accessible by most basidiomycete species.

NON-NUTRITIONAL PARTICLE EXAMPLE

Oat hulls have low starch content and a naturally high lignin content of 14.8% and 5.4% by dry weight respectively. Rice hulls represent a carbon deficient particle, since 67.3% of the material's composition is silicon dioxide. Similarly, buckwheat hulls do not offer starch content and the remaining fiber does not offer the lignin necessary to maintain growths. Cottonseed hulls, which are a byproduct from cottonseed extraction, have an average lignin content in excess of 21% and a starch content of 1.7%.

SUBSTRATE COMPOSITION EXAMPLES

Each of the following substrate compositions composes 5 L volume of dry substrate

| Non-nutritional Particle or Fiber (g) | Nutritional Particle or Fiber (g) | Trace Nutrient (g) | Water (mL) |
|---|---|---|---|
| 335 g Rice Hulls<br>432 g Cottonseed Hulls | 8 g Maltodextrin | 10 g Calcium Sulphate | 1000 mL |
| 450 g Buckwheat Hulls<br>432 g Cottonseed Hulls | 8 g Maltodextrin | 10 g Calcium Sulphate | 1000 mL |
| 335 g Soybean Hulls<br>432 g Cottonseed Hulls | 8 g Maltodextrin | 10 g Calcium Sulphate | 700 mL |
| 300 g Perlite<br>432 g Cottonseed Hulls | 8 g Maltodextrin | 10 g Calcium Sulphate | 1000 mL |
| 520 g Cotton Fiber | 32 g Maltodextrin | 10 g Calcium Sulphate | 1100 mL |
| 480 g Cotton Burs<br>40 g Cottonseed Hulls | 32 g Maltodextrin | 10 g Calcium Sulphate | 800 mL |

As shown in the above table, the ratio of Non-nutritional Particle or Fiber to Nutritional Particle or fiber is at least 15 to 1 (15:1).

Of note, oat hulls are density equivalent and interchangeable with rice hulls and kenaf fiber, hemp pith, sorghum fiber and flax shive are density equivalent and interchangeable with cotton fiber.

Blending substrate, either through stratification or intermixing, can also enhance mycological material characteristics. For example, a low density and elastic modulus substrate (cotton moots) can be applied to external features of a tool while a high density and elastic modulus substrate can be internalized within the material to stiffen the core. An elongated fiber, such as coconut coir, can be positioned along the exterior of a substrate to create a tensile skin to increase surface energy and bolster flexural strength.

Incubation Conditions for Mycological Materials

The incubation environment for the production of mycological materials promotes the continuous production of vegetative tissue (mycelium, "mycelium run") and inhibits primordial formation or fruiting (the production of a basidiocarp or mushroom). Fungal tissue differentiation, physiology and morphology, is dictated through tropisms, which stimulate various growth characteristics based on the surrounding environment. The proposed is two-phase approach that can be implemented in either batch or continuous processing.

In accordance with the method for the production of mycological materials, the engineered substrate is inoculated with a vegetative mycelium as described in the parent patent application and subjected to a two step incubation treatment.

The initial incubation environment at the point of substrate inoculation with the vegetative mycelium is designed to accelerate mycelium run. Full colonization of the substrate can be achieved in as little as four days, and the mycelium can inhibit competitive organisms (mold and bacteria) with metabolic standoff exudates. The environment has an operating relative humidity (RH) of 80-100%, carbon dioxide ($CO_2$) levels that build over the course of the incubation period to be in excess of 5000 ppm, and a temperature between 24 and 30° C. The heightened temperatures support the production of generative hyphae, which achieves rapid colonization but does not offer ideal strength characteristics.

Furthermore, minimizing light exposure or a direct view factor is crucial as light cycling can trigger the fungal circadian rhythm to produce a fruiting body. Reducing the direct light exposure to the mycelium can be achieved with part nesting configurations or ensuring that the light used is outside of the 380 to 500 nm range. Once full colonization is established secondary incubation can be initiated as a finishing step.

The term "full colonization" means, as described in published US Patent Application 2008/0145577 that the vegetative mycelium has grown hyphae that form a network of interconnected mycelia cells through and around the non-nutritional particles of the substrate while digesting the nutritional particles thereby bonding the non-nutritional particles together to form a self-supporting composite material.

The secondary environment can modify any of the following individual growth conditions or a combination thereof depending on the mycelium species and strain:

1. Reducing or maintaining the temperature between 15 and 25° C. This promotes the formation of binding hyphae, which is a different mycelium physiology that offers the optimal strength characteristics for a mycological material. These hyphae are finely branched and non-septate. Basidiocarp formation typically occurs for polypores in temperatures in excess of 21° C., thus fruiting is inhibited and tissue differentiation is predominately within vegetative hyphae.
2. The carbon dioxide levels can be elevated between 10,000 and 60,000 ppm, which is within range for mycelium run and primordial formation, but not for the formation of a fruiting body. The induction of a primordial surface finish (20,000 to 40,000 ppm), which offers a smooth, homogenous surface finish, and superior surface tension strength. The commercial cultivation of mushrooms requires constant air exchanges to maintain an environment containing less than 2000 ppm of $CO_2$.
3. Relative humidity should be elevated to greater than 90%, since the surface area to volume ratio of the nested, pre-colonized materials can be prone to desiccation. Moisture and turgor pressure accelerate mycelium growth and ambient humidity can ensure growth is not hampered. The relative humidity can be passively retained using an open filtered water source or actively with misting through distributed nozzles. This is not an issue with substrate prepared for mushroom production since the trays or bags that house the mycelium culture are either fully enclosed or minimize the surface area to total volume. Furthermore, the relative humidity for mushroom production is typically less than 95% since moisture can activate spores found in mushrooms and result in autolysis.
4. The mycological materials should remain nested in a configuration or environment that offers low or no light exposure.

The invention thus provides an improved method for the production of mycological materials.

What is claimed is:

1. A method of growing basidiomycete mycelium comprising the steps of providing a substrate comprised of non-nutritional material, nutritional particles and nutrient capable of promoting the growth and differentiation of basidiomycete mycelium without supporting the production of a basidiocarp;

adding water to said substrate;

inoculating the substrate with a vegetative mycelium; and thereafter incubating the inoculated substrate in a first incubation period at a temperature between 24 and 30° C., an operating relative humidity of 80 to 100% while allowing carbon dioxide levels to build over the course of incubation to in excess of 5000 ppm and for a period of time sufficient to obtain full colonization of said mycelium within said substrate while minimizing exposure of the inoculated substrate to light to prevent the producing of a basidiocarp.

2. A method as set forth in claim 1 further comprising the step of subjecting the incubated substrate to a secondary incubation period wherein said temperature is maintained between 15 and 25° C. to promote the formation of binding hyphae.

3. A method as set forth in claim 1 further comprising the step of subjecting the incubated substrate to a secondary incubation period wherein said carbon dioxide level is elevated to between 10,000 and 60,000 ppm.

4. A method as set forth in claim 1 further comprising the step of subjecting the incubated substrate to a secondary incubation period wherein said relative humidity is greater than 90%.

5. A method as set forth in claim 1 further comprising the step of subjecting the incubated substrate to a secondary incubation period wherein the incubated substrate is nested in a configuration that offers no light exposure.

6. A method as set forth in claim 1 wherein said non-nutritional material is selected from the group consisting of rice hulls, oat hulls, cottonseed hulls, buckwheat hulls, soybean hulls, perlite, cotton fiber and cotton burs.

7. A method as set forth in claim 1 wherein said nutritional particles are characterized in providing an easily accessible carbon source for said vegetative mycelium.

8. A method as set forth in claim 7 wherein said nutritional particles are selected from the group consisting of simple sugars including dextrose, cellulose and maltose; carbohydrates including maltodextrin and starch; and lignin.

9. A method as set forth in claim 7 wherein said carbon source comprises more than 20% of dry mass of said nutritional particles.

10. A method as set forth in claim 7 wherein said nutritional particles are maltodextrin.

11. A method as set forth in claim 7 wherein said nutrient is calcium sulphate.

12. A method as set forth in claim 1 wherein said substrate comprises 335 g Rice Hulls, 432 g Cottonseed Hulls and 8 g Maltodextrin.

13. A method as set forth in claim 1 wherein said substrate comprises 450 g Buckwheat Hulls, 432 g Cottonseed Hulls and 8 g Maltodextrin.

14. A method as set forth in claim 1 wherein said substrate comprises 335 g Soybean Hulls, 432 g Cottonseed Hulls and 8 g Maltodextrin.

15. A method as set forth in claim 1 wherein said substrate comprises 300 g Perlite, 432 g Cottonseed Hulls and 8 g Maltodextrin.

16. A method as set forth in claim 1 wherein said substrate comprises 520 g Cotton Fiber and 32 g Maltodextrin.

17. A method as set forth in claim 1 wherein said substrate comprises 480 g Cotton Burs, 40 g Cottonseed Hulls and 32 g Maltodextrin.

18. A method as set forth in claim 1 wherein the ratio of said non-nutritional material to said nutritional particles is at least 15 to 1.

* * * * *